United States Patent [19]

Fohler

[11] Patent Number: 4,537,072
[45] Date of Patent: Aug. 27, 1985

[54] ARRANGEMENT FOR EXCHANGING MEASURING AND/OR SAMPLING PROBES

[75] Inventor: Johann Fohler, Puchenau, Austria

[73] Assignee: Voest-Alpine Aktiengesellschaft, Linz, Austria

[21] Appl. No.: 557,356

[22] Filed: Dec. 1, 1983

[30] Foreign Application Priority Data

Dec. 9, 1982 [AT] Austria ................... 4474/82

[51] Int. Cl.³ .............. F27D 21/00; G01N 33/20
[52] U.S. Cl. .................... 73/432 R; 73/864.31; 266/99; 374/140; 901/6
[58] Field of Search ........... 73/432 B, 864.31, 864.59, 73/61 LM; 374/139, 140; 266/99; 136/234; 901/6, 45, 46, 47, 50

[56] References Cited

U.S. PATENT DOCUMENTS 3,948,093 4/1976 Folchi et al. ............. 901/46
4,239,189 12/1980 Scherff ................. 374/140

FOREIGN PATENT DOCUMENTS 36912 6/1980 European Pat. Off. .
2753151 5/1979 Fed. Rep. of Germany ...... 374/140
3044609 6/1982 Fed. Rep. of Germany .
2014728 2/1979 United Kingdom .

Primary Examiner—S. Clement Swisher
Attorney, Agent, or Firm—Brumbaugh, Graves, Donohue & Raymond

[57] ABSTRACT

There is disclosed an arrangement for exchanging measuring and/or sampling probes capable of being slipped on to a holding means arranged on the lower end of a vertically movable lance with friction-tight contact. It includes a grab clamping the probe and movable from an operation position below the lance into a position laterally therebeside. In order to be able to slip on a probe to a holding means assuming a position that deviates from the ideal position, without damage to the holding means and the probes, the grab is mounted on the arrangement by universal joint means.

8 Claims, 6 Drawing Figures

ARRANGEMENT FOR EXCHANGING MEASURING AND/OR SAMPLING PROBES

BACKGROUND OF THE INVENTION

The invention relates to an arrangement for exchanging measuring and/or sampling probes capable of being slipped on to a holding means arranged on the lower end of a vertically movable lance with friction-tight contact, comprising a grab clamping the probe and being movable from an operation position below the lance into a position laterally therebeside.

When carrying out a measuring procedure or taking a sample by immersing a probe into a vessel containing a melt to be observed, for instance a steel works converter, the holding means carrying the probe may be bent, because, for example, the probe is driven against stock not yet melted or pushed against slag parts floating on the molten stock. After retraction of the lance, the probe bent will be in a slanted position deviating from the ideal perpendicular position and thus can no longer be safely seized by the grab.

An additional problem arises when slipping the next probe on to the holding means of the lance by means of the grab, since the probe is held by the grab in a precisely vertical position as rigidly as possible, so as to accommodate the slip-on forces. During slipping on to the holding means of the lance, which, as a rule, is effected by lowering the lance, damage to, or destruction of, the probe by the holding means may occur due to differing positions of the axis of the holding means and of the axis of the probe. For measuring probes, the holding means is designed as a holding rod deeply penetrating into the probe, which near its lower end bar contacts for connecting to the measuring means provided in the probe. When slipping the probe on to the holding rod, damage to the contacts might occur if the probe and the holding rod, are not axially aligned, which may lead to faulty measurements or make measurements impossible.

SUMMARY OF THE INVENTION

The invention aims at avoiding these disadvantages and difficulties and has as its object to provide an arrangement of the initially defined kind, which makes possible to safely slip a probe onto a holding means which is in a position that deviates from the ideal position, wherein damage to the holding means and the probes is avoided and the probes may safely be seized by the grab and perfectly stripped off the lance after having carried out a measurement or sampling.

This object is achieved according to the invention in that the grab is mounted on the arrangement by means of a cardan, or universal joint. Due to the cardanic mounting of the grab, the grab is able to adapt automatically to the position of the probe, or to the position of the holding means, when it is in contact with the measuring probe, or when the probe is in contact with the holding means, respectively.

Suitably, the point of intersection of the axes of the cardanic mounting lies in the axis of the lance, when the grab is in the operation position.

According to a preferred embodiment, the grab is cardanically pivotable out of its resting position against restoring forces, the restoring forces being created either by elastic means or by providing the center of gravity of the grab below the point of intersection of the axes of the cardanic mounting, whereby the grab always automatically resumes its starting position after a grabbing process or after slipping the probe onto the holding means.

In order that the grab assumes a stable position even during slipping on, in particular at the start of slipping on, the holding means gets into friction-tight contact with the probe at a distance below the point of intersection of the axes of the cardanic mounting.

If there is a particularly large deviation of the position of the holding means from the ideal position, it is possible that the lower end of the holding means, which is insertable into the probe, will reach the probe beyond the opening of the probe or will pass by the probe when slipping the probe on to the holding means. In order to prevent this, there is provided according to a preferred embodiment of the invention a centering means arranged at a distance above the grab when in the operation position, which comprises two catch arms movable from a resting position lateral of the holding means int a catch position fixing the holding means in alignment above the grab with the latter in the operation position.

A centering means is known from DE-B-27 53 161. This known centering means enables the adjustment of the lower end of the holding means and of the lance vertically above the probe opening. The centering means includes tracing organs which determine the position coordinates of the holding means and of the probe slipped on to the holding means, whereupon the grab is moved into the thus determined position coordinates. A disadvantage of this known arrangement is to be seen in the fact that a relatively complex coordinate control with similarly complicated controlling organs are required for the drives which move the grab into the desired position.

According to the centering means of the invention, the grab always is moved into the same position for slipping on and for pulling off the probes, and the lance, whose lower end is sufficiently laterally movable (due to the lance being suspended on its upper end), is moved into a position vertically aligned with the grab.

Preferably, the catch arms are designed as superposed sickle-shaped arms and are pivotable from an opened resting position into a catch position embracing the holding means, i.e., by reducing the cross section of the space enclosed by the catch arms to the cross section of the holding means.

Suitably, the centering means is mounted to an arm moving the grab.

BRIEF DESCRIPTION OF THE DRAWINGS

The invention will now be explained in more detail by way of one embodiment and with reference to the accompanying drawings, wherein.

DETAILED DESCRIPTION OF AN EXEMPLARY EMBODIMENT

Figure 1:
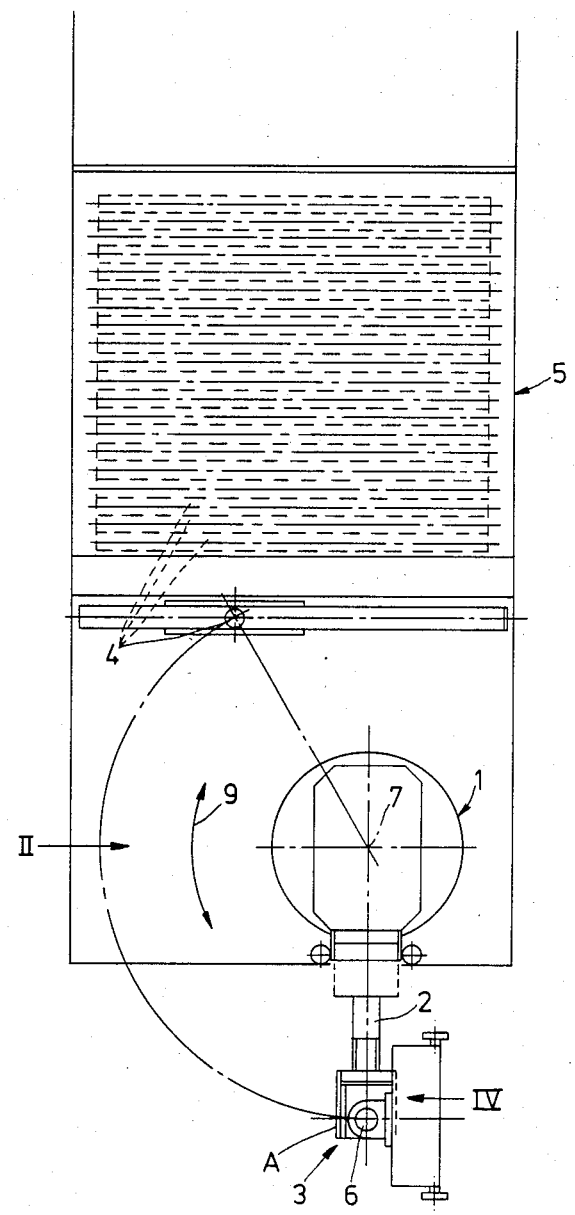
FIG. 1 is a top view of an arrangement for exchanging measuring and/or sampling probes positioned in a steel works.
Figure 2:
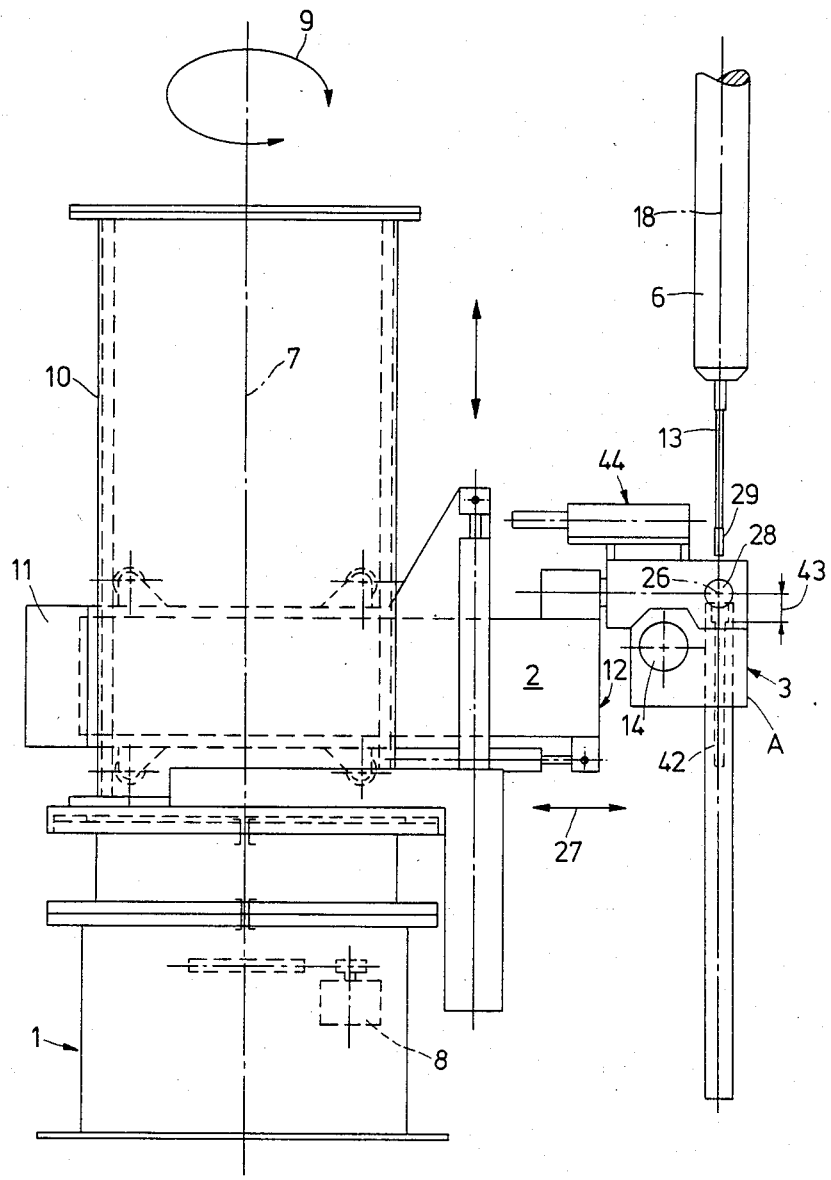
FIG. 2 is a view in the directin of the arrow II of FIG. 1.

Referring to FIGS. 1 and 2, a probe manipulator 1 comprises a grab 3 fastened to an arm 2, to accommodate a probe 4 from a magazine 5 and to transfer this probe 4 to a lance 6 or to remove the probe 4 from the lance 6. The manipulator comprises a column 10 that is rotatable about a vertical axis 7 in the direction of the double arrow 9 by means of a drive 8, a car 11 being mounted on the column so as to be displaceable in the vertical direction. This car 11 serves to accommodate the arm 2, which is displaceable in the horizontal direction and to whose free end 12 the grab 3 clamping the probe 4 is mounted. As is apparent from FIG. 1, the probe 4 can be taken from the magazine 5 by means of the grab 3 by pivoting about the axis 7 and can be placed into a position in alignment with and below the lance 6. By lowering the lance 6, the probe is slipped on to the holding means mounted on the lance and designed as a holding rod 13. To remove the probe 4 from the lance 6, the probe 4 is clamped by the grab 3 and the lance 6 is pulled upwards after having carried out a measurement or sampling, the probe 4 thus being stripped off the holding rod 13, whereupon the probe 4 is taken to a delivery site by means of the grab 3.

Figure 3:
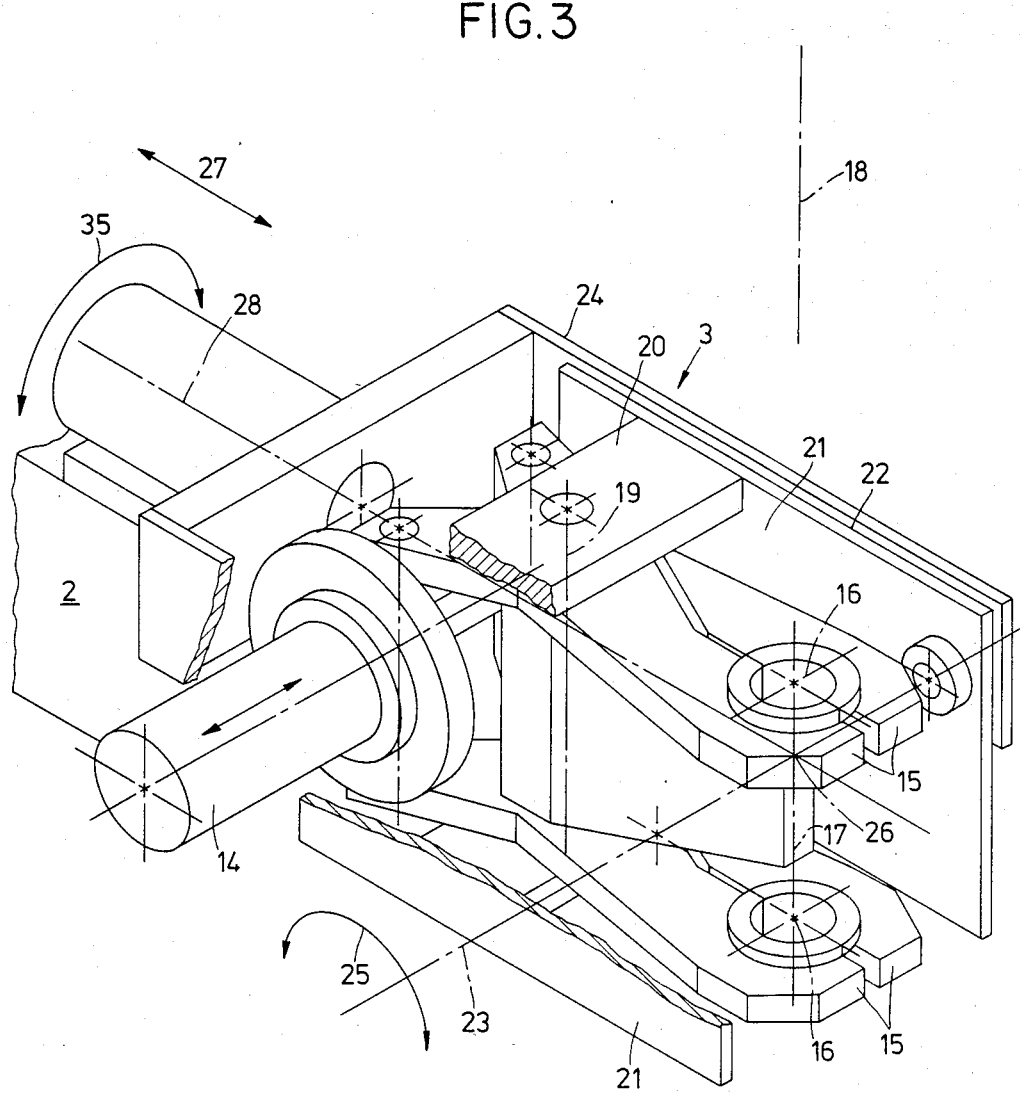
FIG. 3 illustrates a partially sectioned isometric view of the grab.

As shown in FIG. 3, grab comprises two vertically superposed pairs of jaws 15 to be opened and closed by means of a pressure medium cylinder 14, a measuring probe 4 being clampable between their aligning circular recesses 16. An axis 17 is laid through the circular recesses and registers with the axis 18 of the lance 6, with the grab placed in the operation position A (FIGS. 1 and 2). The bearing axle 19 of the jaw pairs 15 is fastened to transverse carriers 20, which form an internal frame 22 with vertical plates 21. The internal frame 22 is mounted so as to be pivotable about a substantially horizontally extending pivot axis 23 relative to an external frame 24 surrounding the internal frame, whereby the jaw pairs 15 and the axis 17 laid through the circular recesses 16 are pivotable relative to the external frame 24 in the direction of the double arrow 25.

The pivot axis 23, which connects the internal frame 22 with the external frame, intersects the axis 17 laid through the circular recesses 16 in a point 26. The external frame 24 is pivotable on the arm 2 about a horizontal axis 28 arranged parallel to the displacement direction 27 of the arm 2 and approximately at a right angle to the pivot axis 23 connecting the external frame 24 with the internal frame 22. This axis 28 intersects with the pivot axis 23 connecting the internal and external frames in the point 26 at which the latter axis is intersected by the axis 17 laid through the circular recess 16.

The axes 23 and 28 constitute a cardanic suspension, or universal joint, mounting the grab 3 so that the axis 17 laid through the circular recesses 16 may be aligned in any direction of space. Thus, the universal joint enables the grab 3 automatically to align the probe 4 with the holding rod 13 of the lance 6, which may obliquely arranged in space, so that damage to the contacts 29 provided on the holding rod is prevented when the probe 4 is slipped on and a perfect seat of the probe 4 on the holding rod 13 is ensured. Any damage to the probe 4 is thereby avoided.

In order that the grab 3 always assumes a stable normal position in its resting state, i.e., without the influence of forces coming from the lance, the external frame 24 is supported relative to the arm 2 by means of a tension rod 30 arranged in a plane perpendicular to the axis 28 (FIGS. 4 and 5), which tension rod is hinged to the external frame 24 on the one hand and to the arm 2 by means of a slide ring 31 on the other hand. On both sides of the slide ring 31, biassed helical springs 32, 33 abut against the same, each being supported, with their ends opposite the slide ring, on supporting plates 34 fastened to the tension rod 30.

Figure 5:
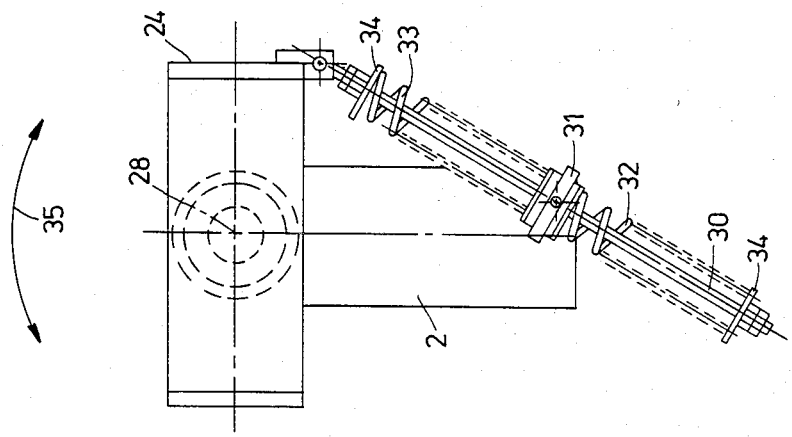
FIG. 5 is a section along line V—V of FIG. 4.

In FIG. 5, the normal position of the external frame 24 relative to the arm 2 is to be seen. As soon as the external frame 24 has been pivoted relative to the arm 2 about the axis 28 in one of the directions of the double arrow 35, one of the springs 32, 33 is compressed and the other spring expands. The unequal spring forces occuring therein act as restoring forces, tending to bring the external frame 24 back into its original normal position after an excursion.

Figure 4:
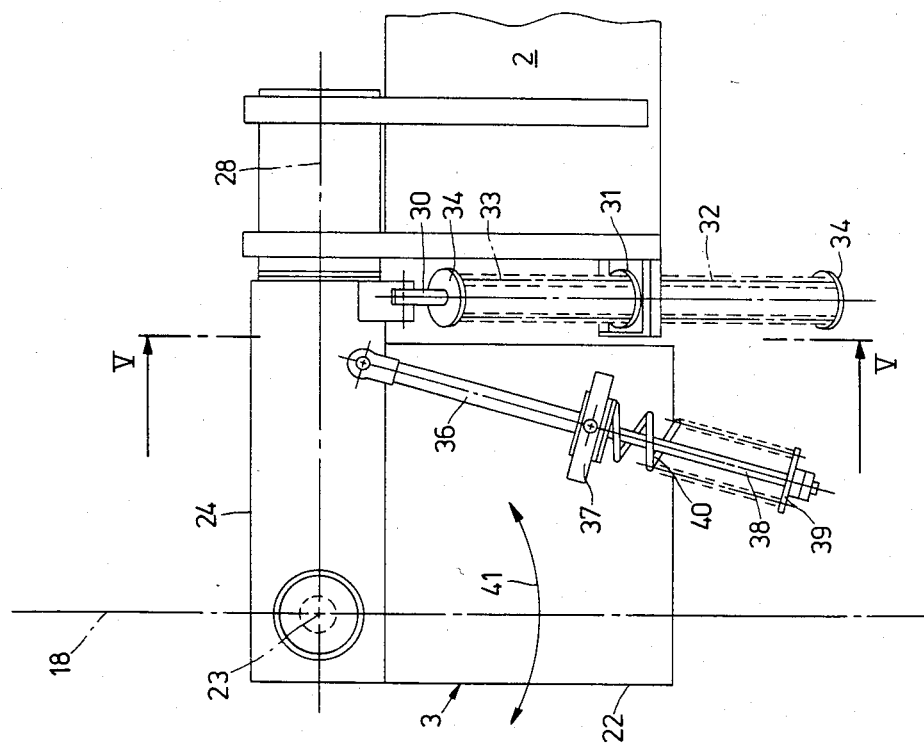
FIG. 4 is a view in the direction of the arrow IV of FIG. 1.

In FIG. 4 the support of the external frame 24 relative to the internal frame 22 is illustrated, wherein a tension rod 36 again is fastened to the external frame 24 on the one hand and to the internal frame 22 by means of a slide ring 37 on the other hand. A helical spring 40 abuts against a supporting plate 39 on an elongation 38 of the tension rod with its opposite end being supported on the slide ring. As soon as the internal frame 22 has been pivoted relative to the external frame 24 in one of the directions of the double arrow 41, the spring 40, which is either compressed or released thereby, tends to return the internal frame to its normal position, in which the spring 40 just balances out the torque stemming from the dead weight of the internal frame 22 plus jaw pairs 15. Instead of the springs 32, 33, 40 pivoting back the grab 3 into its normal position, the grab 3 could be constructed such that the pivot point common to the external frame 24, the internal frame 22 and the jaw pairs 15 (including the pressure medium cylinder 14) comes to lie below the point of intersection 26 of the axes 23 and 28 of the cardanic mounting. In this case, the return of the grab 3 into its normal position would be guaranteed by the dead weight of the grab.

In order to prevent an undesired excursion of the probe 4, and of the axis 17 laid through the circular recesses 16, when threading the holding rod 13 into the opening 42 of the probe 4, the grab 3 is designed such that the holding rod 13 gets into friction-tight contact with the probe at a distance 43 below the point of intersection 26 of the axes 23 and 28 of the cardanic mounting.

Due to unbalanced temperatures to which the lance 6 is subjected within the metallurgical vessel, distortion of the lance 6 may occur so that, after a certain period of operation, the probe holder 13 provided on the lance 6 will no longer be in exact alignment above the probe 4 maintained in the slip-on position by means of the grab 3 pivoted into the operation position A.

Figure 6:
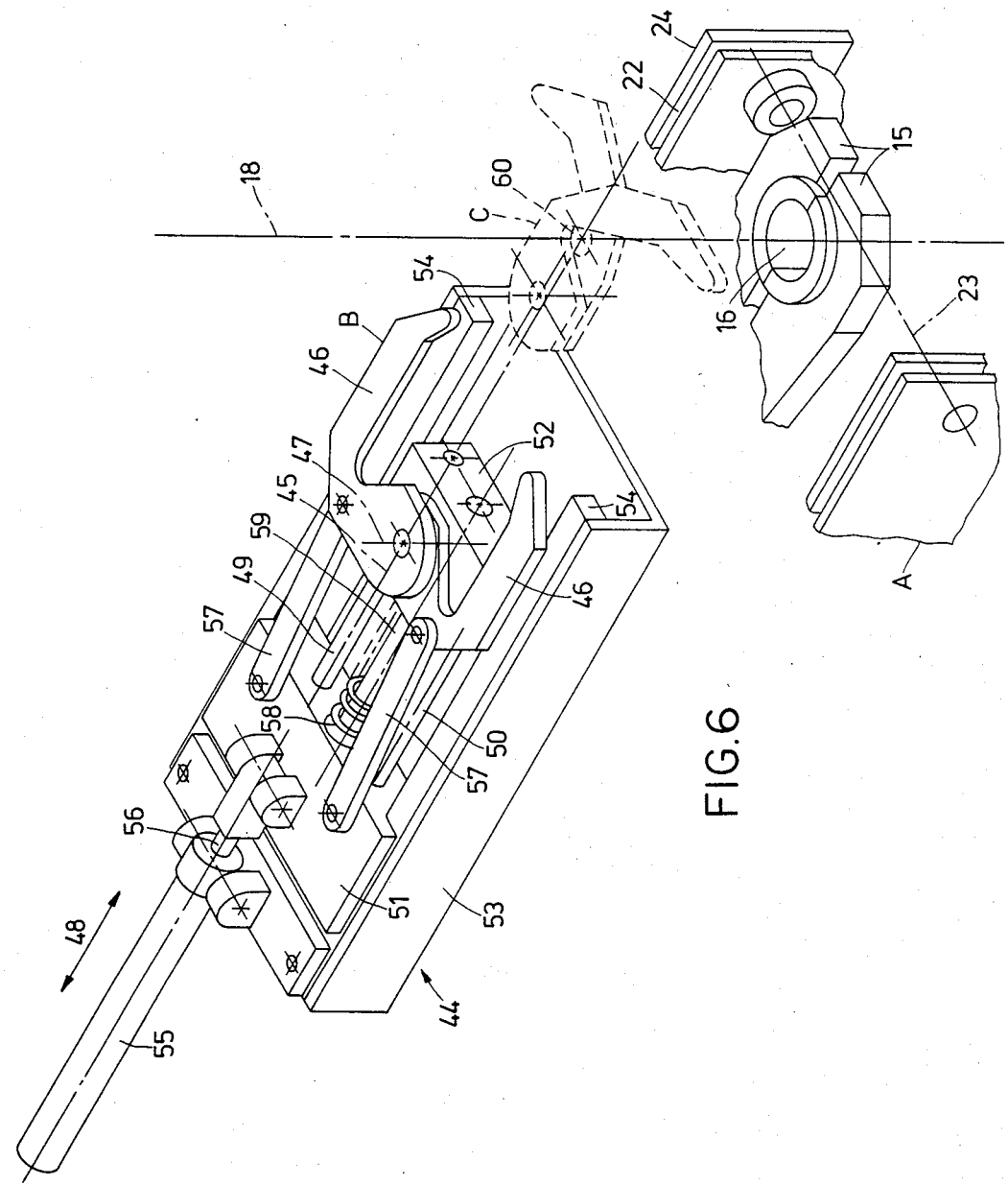
FIG. 6 illustrates an isometric view of a centering means.

In order to be able to ensure the slipping on of the probe 4 to the holding rod in such circumstances, a centering means 44 suitably is provided on the grab 3 above the same. As shown in FIG. 6, this centering means comprises two sickle-shaped catch arms 46 arranged symmetrically to the central axis 45 and pivotable about a pivot axis 47 located in the central axis 45, from a resting position B illustrated in FIG. 6 in full lines into a catch position C illustrated in FIG. 6 in broken lines. The pivot axis 47 common to the two superposed catch arms 46 is provided in a guiding block 52, which is movable in the horizontal direction 48 perpendicular to the lance axis 18 along guiding columns 49, 50 fastened to a sled 51, which is also displaceable horizontally and normal to the axis 18 of the lance 6. Guides 54 arranged in a frame 53 and extending parallel to the guiding columns 49, 50 serve to horizontally guide the sled 51.

A linear drive, which is designed as a pressure medium cylinder 55, is hinged to the frame 53 on the one hand and to the sled 51—by its piston rod 56—on the other hand. The catch arms 46 are connected with the sled 51 by means of straps 57 hinged to them at a distance from the pivot axis 47.

Between the sled 51 and the guiding block 52 a helical spring 58 is under tension, a pin 59 extending parallel to the guides 54 and to the guiding columns 49, 50 serving to secure its position.

The arrangement functions in the following manner:

When the linear drive 55 is actuated, the sled 51, which is shown in the resting position, is displaced along the guides 54 in the direction towards the lance 6, the guiding block 52, which is held at a distance from the sled 51 by the helical spring 58, thus being synchronously displaced together therewith. Thereby the catch arms 46, in the opened state, get into a position above the grab 3, i.e., above the jaw pairs 15.

The movement of the guiding block 52 is stopped by a stop (not illustrated) as soon as it has reached the front end of the frame 53. The sled 51, however, continues to move on under the action of the linear drive 55 so that the distance between the sled 51 and the guiding block 52 is reduced upon compression of the helical spring 58. As a result of the relative movement taking place between the sled 51 and the guiding block 52, the catch arms 46 are moved into the catch position C by means of the straps 57.

As can be seen from FIG. 6, the shape of the catch arms 46 is such that the overlapping catch arms 46, in the catch position C, enclose a free space 60 adapted to the cross section of the part to be caught. According to the embodiment illustrated, this free space is approximately circular and, with respect to its diameter, corresponds to the diameter of the holding rod 13 provided on the lance 6 for the probes 4.

During slipping on of the probe 4 to the holding rod 13, the linear drive 55 is actuated from a certain height of the slip-on movement in order to start the retraction movement of the catch arms 46. Therein, at first only the sled 51 moves along the guides 54 away from the axis 18 of the lance 6, while the guiding block, due to the tension force of the spring 58, initially remains in its foremost position. During this backward movement of the sled 51, the catch arms 46 are being opened. If the end of the spring range has been reached by the sled 51, the sled 51 and the guiding block 52 synchronously move back as far as to the stroke end of the linear drive 55, whereby the catch arms 46 are retracted into position B and thus do no longer restrict the space above the grab.

What I claim is:

1. In an arrangement for exchanging measuring and-/or sampling probes, which probes are slippable onto holding means on the lower end of a verticaly movable lance for frictional engagement therewith, said arrangement including a grab adapted to clamp said probes and movable between an operation position below said lance and a position laterally displaced therefrom, the improvement comprising an arm movable laterally towards and away from said operation position, and
    universal joint means securing said grab to said arm and enabling said grab automatically to align a probe clamped thereby with the holding rod on said lance.

2. An arrangement as set forth in claim 1, wherein said universal joint means has a pair of intersecting axes of rotation and said axes intersect at a point located on the axis of said lance, with said grab being in said operation position.

3. An arrangement as set forth in claim 1, wherein said universal joint means has a pair of intersecting axes of rotation, and further comprising elastic means for creating restoring forces, said grab being pivotable about said axes out of its resting position against said restoring forces.

4. An arrangement as set forth in claim 2, wherein the center of gravity of said grab is below said point of intersection of the axes of said universal joint means so as to create restoring forces, and wherein said grab is pivotable about said axes out of its resting position against said restoring forces.

5. An arrangement as set forth in claim 2, wherein said holding means gets into friction-tight contact with a probe at a distance below said point of intersection of the axes of said universal joint means.

6. An arrangement as set forth in claim 1, further comprising a centering means arranged at a distance above said grab being in said operation position, and wherein said centering means includes two catch arms, said catch arms being movable from a resting position lateral of said holding means into a catch position fixing said holding means in alignment above said grab being in said operation position.

7. An arrangement as set forth in claim 6, wherein said catch arms are designed as sickle-shaped arms arranged above each other and are pivotable from an opened resting position into a catch position enclosing said holding means by reducing the cross section of the space enclosed by said catch arms to the cross section of said holding means.

8. An arrangement as set forth in claim 6, further comprising a grab-moving arm for mounting said centering means.

* * * * *